(12) United States Patent
Gehrig et al.

(10) Patent No.: US 10,131,580 B2
(45) Date of Patent: *Nov. 20, 2018

(54) METHOD FOR PRODUCING A PREFABRICATED BUILDING MATERIAL

(71) Applicant: BASF SE, Ludwigshafen (DE)

(72) Inventors: Uwe Gehrig, Kirchweidach (DE); Ekkehard Jahns, Weinheim (DE); Michael Schinabeck, Altenmarkt an der Alz (DE); Martin Pichler, Kirchweidach (DE); Mehmet Akif Pekmezci, Istanbul (TR); Mehmet Ergin, Istanbul (TR)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/519,891

(22) PCT Filed: Oct. 23, 2015

(86) PCT No.: PCT/EP2015/074619
§ 371 (c)(1),
(2) Date: Apr. 18, 2017

(87) PCT Pub. No.: WO2016/062867
PCT Pub. Date: Apr. 28, 2016

(65) Prior Publication Data
US 2017/0240467 A1    Aug. 24, 2017

(30) Foreign Application Priority Data

Oct. 23, 2014  (EP) .................................. 14190058

(51) Int. Cl.
| | |
|---|---|
| C04B 24/00 | (2006.01) |
| C04B 28/14 | (2006.01) |
| C07C 49/88 | (2006.01) |
| C04B 40/00 | (2006.01) |
| D21H 17/17 | (2006.01) |
| D21H 17/25 | (2006.01) |
| D21H 17/28 | (2006.01) |
| C04B 24/02 | (2006.01) |
| C04B 24/08 | (2006.01) |
| C04B 24/22 | (2006.01) |
| C04B 24/38 | (2006.01) |
| C04B 38/10 | (2006.01) |
| C04B 111/27 | (2006.01) |
| C04B 103/40 | (2006.01) |
| C04B 103/65 | (2006.01) |

(52) U.S. Cl.
CPC .......... *C04B 24/008* (2013.01); *C04B 24/026* (2013.01); *C04B 24/08* (2013.01); *C04B 24/226* (2013.01); *C04B 24/383* (2013.01); *C04B 28/14* (2013.01); *C04B 28/147* (2013.01); *C04B 38/106* (2013.01); *C04B 40/0039* (2013.01); *C07C 49/88* (2013.01); *D21H 17/17* (2013.01); *D21H 17/25* (2013.01); *D21H 17/28* (2013.01); *C04B 2103/40* (2013.01); *C04B 2103/65* (2013.01); *C04B 2111/27* (2013.01); *C04B 2201/20* (2013.01)

(58) Field of Classification Search
CPC ... C04B 24/008; C04B 24/383; C04B 24/226; C04B 24/026; C04B 24/08; C04B 28/147; C04B 38/106; C04B 2103/65; C04B 2103/40; C04B 28/14; C04B 40/0039; C04B 2111/27; C04B 2201/20; D21H 17/17; D21H 17/25; D21H 17/28; C07C 49/88

See application file for complete search history.

(56) References Cited

U.S. PATENT DOCUMENTS

| | | |
|---|---|---|
| 3,307,987 A | 3/1967 | Bieri |
| 3,455,710 A | 7/1969 | Nitzsche et al. |
| 3,935,021 A | 1/1976 | Greve et al. |
| 4,470,877 A | 9/1984 | Johnstone et al. |
| 4,767,457 A | 8/1988 | Ley et al. |
| 5,437,722 A | 8/1995 | Borenstein |
| 5,814,411 A | 9/1998 | Merrifield et al. |
| 5,817,249 A | 10/1998 | Audenaert et al. |
| 5,888,290 A | 3/1999 | Engle et al. |
| 6,001,166 A * | 12/1999 | Ettl ........................ D06M 13/13 106/243 |
| 6,159,339 A | 12/2000 | Hassler et al. |
| 6,165,259 A | 12/2000 | Hallstrom et al. |
| 6,414,055 B1 | 7/2002 | Lauzon |
| 7,078,569 B2 | 7/2006 | Ettl et al. |

(Continued)

FOREIGN PATENT DOCUMENTS

| | | |
|---|---|---|
| AT | 391 131 B | 8/1990 |
| DE | 1 223 287 B | 8/1966 |

(Continued)

OTHER PUBLICATIONS

PCT/EP2015/074619—International Search Report, dated Jan. 12, 2016.
PCT/EP2015/074619—International Written Opinion, dated Jan. 12, 2016.
PCT/EP2015/074619—International Preliminary Report on Patentability, dated Apr. 25, 2017.
PCT/EP2015/074618—International Search Report, dated Jan. 21, 2016.
PCT/EP2015/074618—International Written Opinion, dated Jan. 21, 2016.

(Continued)

*Primary Examiner* — Anthony J Green
(74) *Attorney, Agent, or Firm* — Curatolo Sidoti Co., LPA; Joseph G. Curatolo; Salvatore A. Sidoti

(57) ABSTRACT

The present invention relates to a method for producing a gypsum-containing foamed prefabricated building material and to a gypsum-containing foamed prefabricated building material.

21 Claims, No Drawings

(56) References Cited

U.S. PATENT DOCUMENTS

| | | |
|---|---|---|
| 8,097,124 B2 | 1/2012 | Hamers et al. |
| 2002/0096294 A1* | 7/2002 | Nicholass ............... D21H 17/17 |
| | | 162/179 |
| 2005/0107639 A1 | 5/2005 | Ettl et al. |
| 2005/0250858 A1 | 11/2005 | Wantling et al. |
| 2006/0283356 A1 | 12/2006 | Donlon et al. |
| 2009/0139677 A1* | 6/2009 | Hamers ................. D21H 17/17 |
| | | 162/175 |
| 2010/0116406 A1 | 5/2010 | Mahoney et al. |
| 2014/0202647 A1 | 7/2014 | Hagiopol et al. |
| 2015/0119490 A1 | 4/2015 | Krishnan et al. |
| 2015/0368164 A1* | 12/2015 | Gehrig ................. C04B 24/008 |
| | | 106/203.1 |

FOREIGN PATENT DOCUMENTS

| | | |
|---|---|---|
| EP | 0 223 105 A2 | 5/1987 |
| EP | 418015 A1 * | 9/1990 |
| EP | 1 483 821 B1 | 1/2010 |
| JP | H04100994 A | 4/1992 |
| JP | H05 3055808 A | 11/1993 |
| JP | 2005 281051 A | 10/2005 |
| WO | WO 97/35088 A1 | 9/1997 |
| WO | WO 99/35103 A1 | 7/1999 |
| WO | WO 00/63294 A1 | 10/2000 |
| WO | WO 01/81678 A2 | 11/2001 |
| WO | WO 02/28795 A2 | 4/2002 |
| WO | WO 2004/033581 A1 | 4/2004 |
| WO | WO 2004/108625 A1 | 12/2004 |
| WO | WO 2007/141197 A1 | 12/2007 |
| WO | WO 2010/053494 A1 | 5/2010 |
| WO | WO 2010/112197 A1 | 10/2010 |
| WO | WO 2014/174088 A1 | 10/2014 |

OTHER PUBLICATIONS

Negro, Carlos, et al., "Effects of Flocculants and Sizing Agents on Bending Strength of Fiber Cement Composites", Cement and Concrete Research, 2005, pp. 2104-2109, vol. 35.

Auweter, et al., "Fiber-Optical Quasi-Elastic Light Scattering of Concentrated Dispersions," Journal of Colloid and Interface Science, vol. 105, Issue 2, Jun. 1985, pp. 399-409.

Lilge, et al., "Diffusion in Concentrated Dispersions: A Study With Fiber-Optic Quasi-Elasted Light Scattering (FOQELS)," Colloid and Polymer Science, vol. 269, Issue 7, Jul. 1991, pp. 704-712.

Wiese, et al., "Single Mode Fibers in Fiber Optic Quasielastic Light Scattering: A Study of the Dyanimcs of Concentrated Latex Dispersions," The Journal of Chemical Physics, vol. 94, Issue 10, May 15, 1991, pp. 6429-6443.

Office Action in U.S. Appl. No. 15/519,865, dated Mar. 1, 2018.

\* cited by examiner

METHOD FOR PRODUCING A PREFABRICATED BUILDING MATERIAL

CROSS REFERENCE TO RELATED APPLICATIONS

This application is a national stage application of International Application No. PCT/EP2015/074619, filed 23 Oct. 2015, which claims priority from European Patent Application No. 14190058.9, filed 23 Oct. 2014, which applications are incorporated herein by reference.

The present invention relates to a method for producing a prefabricated building material, in particular to a gypsum-containing foamed prefabricated building material, and to a dispersion for preparing the prefabricated building material.

The construction industry uses a host of different gypsum-containing building materials. The gypsum-containing building materials include gypsums, such as lump gypsums (stucco gypsums), mortar gypsums, machine gypsum plasters, plastering gypsums, adhesion gypsums, jointing gypsums, filling gypsums, stucco gypsums, insulating gypsums, flooring gypsums, ready-mixed plaster gypsums, and imitation marbles. The gypsum-containing building materials further comprise gypsum-containing ready-made structural components, such as gypsum plasterboard panels, gypsum fiberboard panels, gypsum-containing wallboarding panels, insulating gypsum panels, gypsum bricks and gypsum-containing moldings.

Many gypsum-containing building materials have only limited stability on exposure to water. This limited stability is attributable to the water-solubility of the set gypsum. In the outdoor sector, therefore, gypsum is used in impregnated form. In the interior sector, in wet enclosed areas, such as bathrooms or cellars, other building materials are preferentially used.

Industrially, the stability of gypsum-containing building materials with respect to water is increased by hydrophobization. This involves the gypsum-containing building material or its surface being treated with a hydrophobizing agent. Hydrophobizing agents described have included alkyl ketene dimer dispersions (WO 01/81678, U.S. Pat. No. 6,165,259, WO 97/35068), wax emulsions (WO 2010/053494, WO 2004/108625, WO 2004/033581), which may additionally comprise polyvinyl alcohol (US 2010/0116406 A1, U.S. Pat. No. 3,935,021, U.S. Pat. No. 5,437,722) or styrene-(meth)acrylic acid copolymers (WO 00/63294 A1) or combinations of anionic and nonionic surface-active substances (WO 99/35103 A1). Also described as hydrophobizing agents have been water-repellent organosilicon compounds (DE 1223287, U.S. Pat. No. 5,814,411).

Methods for the targeted hydrophobizing of the fiber materials incorporated into gypsum-containing ready-made structural components have also been disclosed. Hydrophobizing agents described in this context include in particular ketene dimers, alkylsuccinic or alkylenesuccinic acid derivatives, polymer-based sizes, alums, and organosilicon compounds (WO 2010/112197), and ketene dimers, alkenyl-succinic anhydrides, and stearic acids (WO 02/28795). According to U.S. Pat. No. 4,470,877, an alkylketene dimer is used as an internal sizing agent for gypsum board paper filled with calcium sulfate dihydrate. PCT/EP2014/058474 discloses a method for producing a gypsum-containing foamed prefabricated building material and to a gypsum-containing foamed prefabricated building material obtainable by this method.

The agents described in the prior art have disadvantages. For instance, certain hydrophobizing agents are not meterable, such as waxes, while others are sensitive to leaching, such as fatty acid derivatives. Anhydrite-bound building materials for facades are rendered hydrophobic using fatty acid salts such as oleates or stearates in powder form. Under the influence of driving rain and frost, in particular, however, the fatty acid salts are leached and broken down.

If a large quantity of hydrophobizing agent has to be added to gypsum in order to set the desired hydrophobicity, this may adversely affect other product properties, such as the strength. The desired hydrophobicity can then not be set independently of other product properties.

The methods known from the prior art are not satisfying for hydrophobizing prior art foamed prefabricated building materials and making them water-resistant. Waxes have to be used in high dilutions and high amounts whereas siloxanes in general exhibit a defoaming action with the consequence that the pore structure of the foam may be adversely influenced.

The problem underlying the present invention is, therefore, that of providing a method for producing a gypsum-containing foamed prefabricated building material that exhibits increased hydrophobicity. A further object on which the present invention is based is that of providing a method for producing a gypsum-containing foamed prefabricated building material that allows an increase in the hydrophobicity using minimal amounts of hydrophobizing agent. Another problem underlying the present invention is that of providing a gypsum-containing foamed prefabricated building material which on exposure to moisture adsorbs only small amounts of water. Further, the method should be simple and should not require a change in the process parameters. Another problem underlying the present invention is to provide a hydrophobized gypsum-containing foamed prefabricated building material which possesses high strength.

Surprisingly it has been found that these objects are achieved by a dispersion comprising an alkyl ketene dimer, a nitrogen containing emulsifier and a formaldehyde condensation product and a method for producing a gypsum-containing foamed prefabricated building material (a gypsum-containing foamed ready-made structural component) by contacting gypsum hemihydrate or anhydrite with said dispersion.

The invention therefore relates to a method for producing a gypsum-containing foamed prefabricated building material (a gypsum-containing foamed ready-made structural component).

Embodiments of the invention are as follows:

1. A method for producing a gypsum-containing foamed prefabricated building material
   (i) providing an aqueous alkyl ketene dimer dispersion (AKD dispersion) comprising
   (a) an alkyl ketene dimer of the formula (I)

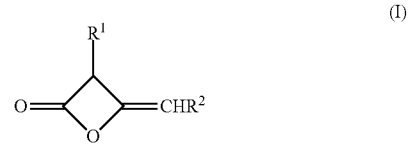

and/or of the formula (II)

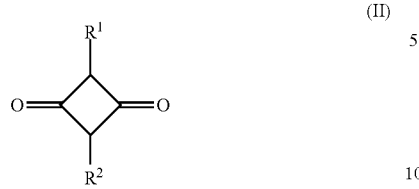

in which
R¹ and R² are identical or different hydrocarbon radicals comprising 10 to 24 carbon atoms;
(b) at least one emulsifier having a nitrogen content ≤1% by weight selected from the group consisting of a starch, cellulose, starch derivative or cellulose derivative;
(c) a condensation product of phenol sulfonic acid and formaldehyde, naphthalene sulfonic acid and formaldehyde or naphthalene sulfonic acid, phenol, formaldehyde and urea wherein the sulfonic acid groups may optionally be present in protonated or deprotonated or partly in protonated and partly in deprotonated form;
wherein the dispersion has a charge density in the range from −5 to −150 µeq/g.;
(ii) adding a foam and gypsum hemihydrate or anhydrite or a mixture thereof, to obtain a gypsum composition and
(iii) forming, optionally curing and drying the gypsum composition to obtain the foamed prefabricated building material.
2. The method according to embodiment 1, wherein the hydrocarbon radicals in formula I or II are selected from branched and unbranched $C_{12}$-$C_{24}$-alkyl or $C_{12}$-$C_{24}$-alkenyl.
3. The method according to embodiment 1 or 2, wherein the hydrocarbon radicals are selected from branched and unbranched $C_{12}$-$C_{24}$-alkyl, more particularly branched and unbranched $C_{14}$-$C_{20}$-alkyl, and more preferably branched and unbranched $C_{16}$-$C_{18}$-alkyl, such as branched and unbranched $C_{16}$-alkyl and branched and unbranched $C_{18}$-alkyl.
4. The method according to any of the preceding embodiments, wherein the AKD dispersion additionally comprises at least one fatty alcohol alkoxylate, fatty amine alkoxylate or fatty acid alkoxylate.
5. The method according to embodiment 4, wherein the AKD dispersion additionally comprises at least one fatty alcohol alkoxylate.
6. The method according to embodiment 4 or 5, wherein the fatty alcohol and the fatty acid comprise 8 to 18 carbon atoms.
7. The method according to any of embodiments 4 to 6, wherein the alkoxylate is a $C_2$-$C_4$ alkoxylate, in particular ethoxylate and/or propoxylate.
8. The method according to any of embodiments 4 to 7, wherein the alkoxylate comprises 5 to 30, in particular 10 to 20 alkoxy groups.
9. The method according to any of the preceding embodiments, wherein the emulsifier is a starch derivative.
10. The method according to any of the preceding embodiments, wherein the emulsifier has a nitrogen content in the range from 0.05 to 1% by weight, in particular 0.2 to 0.8% by weight.
11. The method according to any of the preceding embodiments, wherein the emulsifier has a Brookfield viscosity in a 10% w/w aqueous solution (RVDV-II+PX, spindle 01, 6 rpm, 20° C.) in the range from about 3 to about 200 mPas, in particular in the range from about 10 to about 200 mPas or about 10 to about 100 mPas.
12. The method according to any of the preceding embodiments, wherein the AKD dispersion is prepared by adding the alkyl ketene dimer in the form of an aqueous precursor dispersion or in solid form, in particular in powder form, to components (b) and (c).
13. The method according to any of the preceding embodiments, wherein the gypsum hemihydrate or anhydrite is employed in solid form or in the form of an aqueous suspension.
14. The method according to any of the preceding embodiments, wherein the aqueous AKD dispersion comprises 1 to 60 wt %, preferably 5 to 50 wt %, more particularly 10 to 45 wt %, of ketene dimer, based on the total weight of the dispersion.
15. The method according to any of the preceding embodiments, wherein the aqueous AKD dispersion comprises 1 to 15 wt %, preferably 1 to 10 wt %, more particularly 2 to 8 wt %, of emulsifier, based on the overall solids content of the dispersion.
16. The method according to any of the preceding embodiments, wherein the aqueous AKD dispersion comprises aluminium sulfate, in particular 0.1 to 10 wt %, preferably 0.1 to 7.5 wt %, and in particular 0.2 to 5 wt % of aluminium sulfate, based on the ketene dimer.
17. The method according to any of the preceding embodiments, wherein the aqueous AKD dispersion has a charge density in the range from −20 to −120 µeq/g, in particular −30 to −100 µeq/g.
18. The method according to any of the preceding embodiments, wherein the weight ratio of ketene dimer to said condensation product is in the range from 200:1 to 5:1, in particular 100:1 to 10:1.
19. The method according to any of embodiments 4 to 18, wherein the aqueous AKD dispersion comprises 0.1 to 3 wt %, preferably 0.2 to 2 wt %, more preferably 0.2 to 1.5 wt % of said fatty alcohol alkoxylate, fatty amine alkoxylate or fatty acid alkoxylate, based on the overall solids content of the dispersion.
20. The method according to any of embodiments 4 to 19, wherein the weight ratio of ketene dimer to said fatty alcohol alkoxylate, fatty amine alkoxylate or fatty acid alkoxylate is in the range from 500:1 to 10:1, in particular 200:1 to 10:1.
21. The method according to any of the preceding embodiments, wherein the aqueous AKD dispersion comprises a wax, in particular a paraffin wax.
22. The method according to embodiment 25, wherein the aqueous AKD dispersion comprises 2 to 40 wt %, in particular 5 to 30 wt %, of the wax.
23. The method according to embodiments 221 or 22, wherein the weight ratio of ketene dimer to said wax is in the range from 9:1 to 1:9.
24. The method according to any of the preceding embodiments, wherein the aqueous AKD dispersion has a pH in the range from 3 to 9, preferably 4 to 9, in particular 4 to 8.
25. The method according to any of embodiments 14 to 23, wherein the disperse phase of the aqueous precursor ketene dimer dispersion has an average diameter of <10 µm, preferably <5 µm, more preferably <3 µm and in particular <2 µm, with the lower limit being 0.5 µm.

26. The method according to any of the preceding embodiments, wherein the aqueous AKD dispersion comprises an organic solvent.
27. The method according to any of the preceding embodiments, wherein the ketene dimer is used in an amount of 0.02 to 8, preferably 0.1 to 5, more particularly 0.2 to 3 wt %, based on the mass of gypsum hemihydrate or anhydrite.
28. The method according to any of the preceding embodiments, wherein one or more additives are additionally added to the AKD dispersion which additives are selected from cellulose ethers, slaked lime, mineral additives, low-density aggregates, fibers, fiber-containing components, starch, modified starch, accelerators, thickeners, retarders, air entrainers, foaming agents, antifoam additives, swelling agents, fillers, polyacrylates, dispersants, plasticizers, superabsorbents, and stabilizers.
29. The method according to embodiment 28, wherein the one or more additives are selected from fibers and fiber-containing components.
30. The method according to embodiment 28 or 29, wherein the additive(s) is (are) added during or after step (ii).
31. The method according to any of the preceding embodiments, wherein the gypsum hemihydrate or anhydrite is selected from α-hemihydrate, α/β-hemihydrate, β-hemihydrate, anhydrite obtained from flue gas desulfurization or natural source, natural anhydrite, synthetic anhydrite and/or mixtures of two or more thereof.
32. The method according to embodiment 31, wherein the gypsum is selected from β-hemihydrate, anhydrite obtained from flue gas desulfurization or natural source, and/or mixtures thereof.
33. The method according to any of the preceding embodiments, wherein an aqueous foam having a density from 50 to 300 g/l, preferably 60 to 250 g/l, is used.
34. The method according to any of the preceding embodiments, wherein a surfactant-based, preferably an anionic, non-ionic or amphoteric surfactant-based aqueous foam is used and/or mixtures thereof.
35. The method according to embodiment 34, wherein an aqueous foam based on $C_6$-$C_{20}$ alkylsulfate or $C_6$-$C_{20}$ alkylethersulfate is used.
36. The method according to any of the preceding embodiments, wherein the amount of foam is such that the amount of surfactant is ≤2 g, preferably 0.01 to 1 g, per kg gypsum hemihydrate or anhydrite.
37. The method according to any of the preceding embodiments, wherein the gypsum containing foamed prefabricated building material has a core density of 0.4 to 1.1, preferably 0.4 to 0.9 and more preferably 0.5 to 0.8 kg/dm$^3$.
38. The method according to any of the preceding embodiments, wherein the gypsum hemihydrate or anhydrite treated with the ketene dimer is subjected to a heat treatment.
39. The method according to embodiment 38, wherein the heat treatment takes place at a temperature in the range from 40 to 110° C., more particularly 50 to 100° C., and preferably 60 to 90° C.
40. The method according to any of the preceding embodiments, wherein the gypsum hemihydrate or anhydrite is admixed with the AKD dispersion or a part thereof and the aqueous foam is then added to the mixture.
41. The method according to any of embodiments 1 to 43, wherein the gypsum hemihydrate or anhydrite is admixed with the aqueous foam or a part thereof and the ketene dimer is added to the mixture.
42. The method according to any of the preceding embodiments, wherein the aqueous AKD dispersion comprises aluminium sulfate.
43. The method according to embodiment 42, wherein the aqueous AKD dispersion comprises 0.1 to 10 wt %, preferably 0.1 to 7.5 wt %, and in particular 0.2 to 5 wt % of aluminium sulfate, based on the ketene dimer.
44. The method according to any of the preceding embodiments, wherein the AKD dispersion is prepared by adding component (c) to component (b) in an amount such that the dispersion has a charge density in the range from −5 to −150 μeq/g and then adding the alkyl ketene dimer.
45. An aqueous alkyl ketene dimer dispersion (AKD dispersion) comprising
(a) an alkyl ketene dimer of the formula (I)

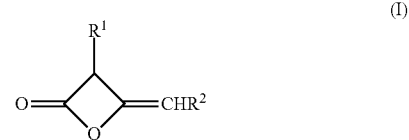

and/or of the formula (II)

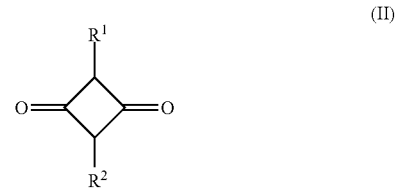

in which
R$^1$ and R$^2$ are identical or different hydrocarbon radicals comprising 10 to 24 carbon atoms;
(b) at least one emulsifier having a nitrogen content ≤1% by weight selected from the group consisting of a starch, cellulose, starch derivative or cellulose derivative;
(c) a condensation product of phenol sulfonic acid and formaldehyde, naphthalene sulfonic acid and formaldehyde or naphthalene sulfonic acid, phenol, formaldehyde and urea wherein the sulfonic acid groups may optionally be present in protonated or deprotonated or partly in protonated and partly in deprotonated form;
wherein the dispersion has a charge density in the range from −5 to −150 μeq/g.
46. The dispersion of embodiment 45 having a charge density in the range from −10 to −120 μeq/g, in particular −20 to −100 μeq/g.
47. The dispersion of embodiment 45 or 46, wherein the at least one emulsifier has a nitrogen content in the range from 0.05 to 1% by weight, in particular 0.2 to 0.8% by weight and/or wherein the emulsifier has a Brookfield viscosity in a 10% w/w aqueous solution (RVDV-II+PX, spindle 01, 6 rpm, 20° C.) in the range from about 3 to about 200 mPas, in particular in the range from about 10 to about 200 mPas or about 10 to about 100 mPas.
48. The dispersion of any of embodiments 45 to 47, wherein the emulsifier has a nitrogen content in the range from 0.05 to 1% by weight, in particular 0.2 to 0.8% by weight.
49. The dispersion of any one of the preceding embodiments which additionally comprises at least one fatty alcohol alkoxylate, fatty amine alkoxylate or fatty acid alkoxylate.

50. The dispersion of embodiment 49, wherein the fatty alcohol alkoxylate is a $C_8$-$C_{18}$ alkanol ethoxylate with 10 to 30 ethylene oxide groups.
51. The dispersion of any one of embodiments 45 to 50 which additionally comprises a wax.
52. The dispersion of any one of embodiments 45 to 51 in the form of a gypsum composition which dispersion additionally comprises gypsum hemihydrate or anhydrite or a mixture thereof.
53. The dispersion of embodiment 52, wherein the gypsum hemihydrate or anhydrite is selected from α-hemihydrate, α/β-hemihydrate, β-hemihydrate, natural anhydrite, synthetic anhydrite, anhydrite obtained from flue gas desulfurization, and/or mixtures of two or more thereof.
54. The dispersion of any one of embodiments 45 to 53 which additionally comprises an aqueous foam.
55. The dispersion of embodiment 54, wherein a foam having a density from about 50 to 300 g/l, in particular 60 to 250 g/l, is used.
56. The dispersion of embodiment 55, wherein the foam is obtainable from 0.01 to 2 g surfactant per kg gypsum hemihydrate or anhydrite.
57. The dispersion of any one of embodiments 45 to 56 comprising 1 to 60 wt %, preferably 5 to 50 wt %, more particularly 10 to 45 wt %, of ketene dimer, based on the total weight of the dispersion.
58. The dispersion of any one of embodiments 45 to 57 comprising 1 to 15 wt %, preferably 1 to 10 wt %, more particularly 2 to 8 wt %, of emulsifier, based on the overall solids content of the dispersion.
59. The dispersion of any one of embodiments 45 to 58 comprising 0.1 to 3 wt %, preferably 0.2 to 2 wt %, more preferably 0.2 to 1.5 wt % of said fatty alcohol alkoxylate, fatty amine alkoxylate or fatty acid alkoxylate, based on the overall solids content of the dispersion.
60. The dispersion of any one of embodiments 45 to 59 comprising 10 to 20 wt % of the wax.
61. An aqueous dispersion as defined in any one of embodiments 1 to 44.
62. A prefabricated building material, in particular a gypsum-containing foamed prefabricated building material, comprising a foamed gypsum body hydrophobized with a dispersion as defined in any one of embodiments 54 to 61.
63. A gypsum-containing foamed prefabricated building material obtainable by the method according to any one of embodiments 1 to 44.
64. The prefabricated building material of embodiment 62 or 63, wherein the gypsum body has a core density of 0.4 to 1.1 kg/dm³, preferably 0.4 to 0.9 and more preferably 0.5 to 0.8 kg/dm³.
65. The prefabricated building material according to any one of embodiment 62 to 64, which is selected from panels, rods, and pipes.
66. The prefabricated building material according to embodiment 65, which is selected from gypsum plasterboard panels, gypsum fiberboard panels, gypsum-containing wallboarding panels, sheathing products and gypsum-containing moldings.
67. The prefabricated building material according to any one of embodiments 62 to 66, which comprises fibers or a fiber-containing component.
68. The prefabricated building material according to embodiment 67, wherein the fiber-containing component is a paper, glass fibers, a woven or non-woven glass or a card.
69. The prefabricated building material according to embodiment 68, wherein the fiber-containing component is present on at least one of the surfaces of the prefabricated building material or incorporated parallel to at least one of the surfaces into the prefabricated building material.
70. The prefabricated building material according to any of embodiments 67 to 69, wherein the fiber-containing component comprises macroscopic fibers in netlike disposition or microscopic fibers in sheet-like distribution.
71. The prefabricated building material according to any of embodiments 67 to 69, wherein the fibers are cellulose fibers and the fiber-containing component comprises cellulose fibers.

The invention relates to a method for producing a gypsum-containing foamed prefabricated building material comprising the steps of
(i) providing an alkyl ketene dimer dispersion comprising
(a) an alkyl ketene dimer of the formula (I)

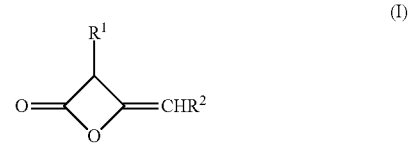

and/or of the formula (II)

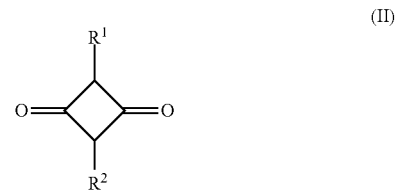

in which
$R^1$ and $R^2$ are identical or different hydrocarbon radicals comprising 10 to 24 carbon atoms;
(b) at least one emulsifier having a nitrogen content of ≤1% by weight selected from the group consisting of a starch, cellulose, starch derivative or cellulose derivative;
(c) a condensation product of phenol sulfonic acid and formaldehyde, naphthalene sulfonic acid and formaldehyde or naphthalene sulfonic acid, phenol, formaldehyde and urea wherein the sulfonic acid groups may optionally be present in protonated or deprotonated or partly in protonated and partly in deprotonated form;
wherein the dispersion has a charge density in the range from −5 to −150 μeq/g.;
(ii) adding a foam and gypsum hemihydrate or anhydrite or a mixture thereof, to obtain a gypsum composition and
(iii) forming, optionally curing and drying the gypsum composition to obtain the foamed prefabricated building material.

The hydrocarbon radicals are selected preferably from branched and unbranched $C_{12}$-$C_{24}$-alkyl or $C_{12}$-$C_{24}$-alkenyl; more preferably from branched and unbranched $C_{12}$-$C_{24}$-alkyl; and very preferably from branched and unbranched $C_{14}$-$C_{20}$-alkyl. With very particular preference the hydrocarbon radicals are selected from branched and unbranched $C_{14}$-, $C_{15}$-, $C_{16}$-, and $C_{18}$-alkyl. By "alkenyl" are meant branched and unbranched, ethylenically unsaturated aliphatic hydrocarbons having one, two, or three double bonds.

"Gypsum hemihydrate" or "anhydrite" is a calcium sulfate-containing binder which is capable of forming calcium sulfate dihydrate. The gypsum hemihydrate or anhydrite contains at least 65 wt. %, preferably, at least 80 wt. %, in particular at least 90 and especially at least 95 wt. %, of hemihydrate or anhydrite with the remainder being calcium sulfate dihydrate and/impurities depending on the origin of the hemihydrate or anhydrite. The hemihydrate or anhydrite is selected more particularly from α-hemihydrate, α/β-hemihydrate, β-hemihydrate (β-hemihydrate which is synthetic or obtained from natural sources), natural anhydrite, synthetic anhydrite, anhydrite obtained from flue gas desulfurization, and/or mixtures of two or more thereof; preferably from β-hemihydrate (more particularly β-hemihydrate obtained from natural sources), anhydrite obtained from flue gas desulfurization, and/or mixtures thereof. The term "gypsum" also refers here, however, to the dihydrate, since the alkyl ketene dimer can also be applied, for imparting water repellency, to the surface of gypsum that has already set. The term "gypsum" also refers here to a mixture of the calcium sulfate-containing binder with other components, more particularly components for the production of gypsum-containing ready-made structural components.

"Hydrophobized" as used herein means that the water uptake of a gypsum-based material is ≤25%, preferably ≤10% and more preferably ≤5%, in accordance with DIN EN 520.

The gypsum hemihydrate or anhydrite may be contacted in solid form or in the form of an aqueous suspension with the AKD dispersion. The gypsum hemihydrate or anhydrite is usefully mixed in solid form with the ketene dimer suspension, being introduced into the aqueous ketene dimer dispersion, for example. If the gypsum hemihydrate or anhydrite is employed in the form of an aqueous suspension, the AKD dispersion is usefully introduced into the gypsum suspension. This introduction of the AKD dispersion takes place within a period of up to one minute after the preparation of the gypsum hemihydrate or anhydrite suspension. The amounts of water are selected such that contacting of ketene dimer and gypsum produces a ready-to-use gypsum slurry which at this stage contains at least in part gypsum dihydrate. In order to ensure uniform distribution of the ketene dimer in the gypsum, homogenization takes place using customary apparatus, as for example stirring apparatus, such as Hobart mixers.

The ketene dimer is obtained by dimerization of ketenes. The ketenes are prepared, for example, by reaction of carbonyl chlorides with tertiary amines. Of particular technical importance are carbonyl chlorides which are obtainable by chlorination of naturally occurring fatty acids or mixtures thereof, examples being acid chlorides based on fatty acids got from coconut oil, tall oil, castor oil, olive oil, bovine tallow, or palm kernel oil. Typical examples of carbonyl chlorides are myristoyl chloride, palmitoyl chloride, stearoyl chloride, oleoyl chloride, behenoyl chloride, and isostearoyl chloride. The reaction of the carbonyl chlorides with the tertiary amines is conducted with particular advantage in the absence of solvents, with thorough mixing, at temperatures of 65 to 150° C. in accordance with the method known from EP-A 1 453 821.

According to the invention it has surprisingly been found that the use of the AKD dispersion as defined above imparts improved hydrophobicity to the gypsum-containing foamed prefabricated building material. Emulsifiers having a nitrogen content in the range from 0.05 to 1% by weight as determined by elemental analysis are low to highly cationically modified emulsifiers. Suitable emulsifiers are low to highly cationically modified starches and celluloses and derivatives thereof with starches and derivatives thereof being preferred. Low cationically modified emulsifiers have a nitrogen content from 0.05 to 0.18% by weight whereas high cationically modified emulsifiers have a nitrogen content from 0.2 to 1% by weight. Preferred starches and celluloses are those modified by ammonium structural units. Cationic starch and cationic cellulose contemplated comprises all water-soluble starches and water-soluble celluloses that have an amino group and/or ammonium group as cationic group. Such starches are available commercially. They are obtained, for example, by reaction of native starch with compounds which have tertiary or quaternary nitrogen atoms, such as alkylaminoalkyl epoxides or alkylaminoalkyl chlorides. Examples of such compounds are 3-chloro-2-hydroxypropyltrimethylammonium chloride and glycidyltrimethylammonium chloride.

Preferred low cationic starches have ammonium structural units which are identical or different and conform to the formula (IIIa) and/or the formula (IIIb)

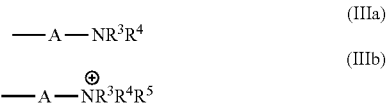

in which
A is branched or unbranched $C_1$-$C_4$-alkylene which is optionally substituted by one or more hydroxyl or phenyl groups; or
A is $C_1$-$C_3$-alkylene-phenylene, phenylene-$C_1$-$C_3$-alkylene, or $C_1$-$C_3$-alkylene-phenylene-$C_1$-$C_3$-alkylene which is optionally substituted by one or more hydroxyl groups; and
$R^3$, $R^4$, and $R^5$ independently of one another are branched or unbranched $C_1$-$C_4$-alkyl or $C_2$-$C_4$-hydroxyalkyl, it also being possible for $R^5$ to be H.

Preference is given to the ammonium structural units which are identical or different and conform to the formula (IIIb) in which
A is —CH$_2$—CHOH—CH$_2$—, —CH$_2$—CH(CH$_2$OH)—, or —CH$_2$—CH$_2$—; and
$R^3$, $R^4$, and $R^5$ independently of one another are methyl or ethyl.

In one preferred embodiment the ammonium structural units conform to the formula (IV).

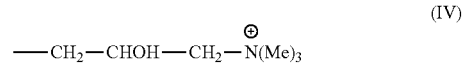

A low cationic starch or low cationic cellulose may also be a low cationic degraded starch or cellulose. Degraded starches and celluloses are obtainable by subjecting a native starch or cellulose first to a degradation procedure in order to reduce the molecular weight of the starch or cellulose to give a Brookfield viscosity (20° C.; spindle 61 or 62; 12 rpm) in the range from about 10 to about 500 mPas in a 10% w/w aqueous solution, and then cationizing the degraded starch or cellulose. The degradation may take place oxidatively, thermally, hydrolytically and/or enzymatically. An example for a low cationic starch of the invention is Amylex KLP commercially available from Südstärke.

Emulsifiers according to the invention may also be nonionic degraded starches and celluloses and modified degraded starches and celluloses such as degraded alkylated and hydroxyalkylated starches and celluloses. Examples for suitable nonionic emulsifiers are Amylex 15 or Amylex 20/20 available from Südstärke.

A highly cationic starch or highly cationic cationic cellulose may also be a highly cationized degraded starch or cellulose. The latter are obtainable by subjecting a native starch or cellulose first to a degradation procedure in order to reduce the molecular weight of the starch or cellulose, and then cationizing the degraded starch or cellulose. The degradation may take place oxidatively, thermally, hydrolytically and/or enzymatically.

The degree of substitution of the highly cationic cationic starch is preferably 0.1 to 0.5 and more preferably in the range from 0.2 to 0.4.

A suitable basis for cationic starches comprises, for example, starches from potatoes, tapioca, rice, wheat, corn, sorghum, and peas. The amylopectin content of starches may amount for example to 0.1% to 100%. One example of a highly cationic cationic starch is Percole® 134 EP, with a degree of substitution of 0.17. Particularly preferred is cationic potato starch which is modified with a tertiary amine or with a quaternary amine and has a viscosity of 50 to 200 mPas (measured in a Brookfield viscometer at a temperature of 20° C., spindle 2, with a solids content of 3.0%). An example for a high cationic starch of the invention is Hi-Cat from Roquette (nitrogen content of about 0.3% by weight.

According to the invention it has surprisingly been found that the use of an AKD dispersion containing a condensation product of phenol sulfonic acid or naphthalene sulfonic acid and formaldehyde or a condensation product of phenolsulfonic acid, phenol, formaldehyde and urea results in improved hydrophobicity of the gypsum-containing foamed prefabricated building material. Such condensation products are commercially available from BASF SE. Examples are Tamol® DN or Tamol® NN7718.

In addition, it has surprisingly been found that the use of an AKD dispersion containing a solvent selected from fatty alcohol alkoxylates, fatty amine alkoxylates or fatty acid alkoxylates even further improves the hydrophobicity of the gypsum-containing foamed prefabricated building material. Fatty alcohol alkoxylates, in particular fatty alcohol ethoxylates are preferred. Suitable solvents are available from BASF SE, for example Degressal SD 21.

Furthermore, it has surprisingly been found that the ketene dimer can be partially replaced by a wax, in particular a paraffin wax, without impairing hydrophobicity and setting properties of the gypsum composition.

The AKD dispersion of the invention may additionally be stabilized by a dispersant, preferably by a protective colloid. The protective colloid may be nonionic, or amphoteric, and is selected more particularly from synthetic, natural, and modified natural polymers.

Examples of suitable nonionic protective colloids are polyvinyl alcohol, polyvinylpyrrolidone and copolymers containing vinylpyrrolidon, hydroxypropylcellulose, or hydroxypropylmethylcellulose, etc. A list of suitable protective colloids is published in Houben-Weyl, Methoden der organischen Chemie, Band XIV/1, Makromolekulare Stoffe, Georg-Thieme-Verlag, Stuttgart, 1961, S. 411 bis 420.

Examples of suitable amphoteric protective colloids are proteins, such as gelatine.

Employed with particular preference are the aforementioned nonionic colloids.

The aqueous AKD dispersion preferably comprises 1 to 60 wt %, more particularly 5 to 50 wt %, and more preferably 10 to 45 wt %, of ketene dimer. The aqueous AKD dispersion preferably further comprises 0.1 to 10 wt %, more preferably 0.1 to 7.5 wt % and in particular 0.2 to 5 wt % of aluminium sulfate, based on the ketene dimer.

In the AKD dispersion component (c) is used in an amount such that the dispersion has a charge density in the range from −5 to −150 µeq/g, preferably in the range from −10 to −120 µeq/g, in particular −20 to −100 µeq/g. Thus, the condensation product (c) is in general present in an amount of 0.1 to 5 wt %, preferably 0.5 to 4 wt % and in particular 1 to 3 wt %, based on the total weight of the AKD dispersion.

The charge density of the dispersion is determined with a coulometer (Mütek PCD 04) at pH 3.5 with a 0.001 moL/L Poly-DADMAC-solution (polydiallyldimethyl ammoniumchloride, commercially available, for example from Sigma-Aldrich) for anionic surfaces and 0.001 mol/L Sodium polyethylene sulfonate for cationically charged particle surfaces. From each sample an amount of 1-2 grams is taken and diluted with Soerensen buffer solution (mixture of citrate buffer and 0.1 mol/L HCl, Ref.: "Chemische Tabellen und Rechentafeln für die analytische Praxis", Rauscher/Voigt/Wilke/Wilke, p. 141) to a volume of 100 mL. A sample of 10 mL solution is used for the measurement. As a result, the charge density is obtained as µeq/g dispersion.

The aqueous AKD dispersion preferably has a pH of 3 to 9, preferably 5 to 9.

The aqueous AKD dispersions which comprise aluminium sulfate preferably also comprise at least one acid selected from saturated $C_1$-$C_{10}$ carboxylic acids, benzenesulfonic acid, p-toluenesulfonic acid, and mineral acids ($H_2SO_4$, $H_3PO_4$). The acid is preferably present in an amount of 0.5 to 5 wt %, based on the ketene dimer.

The ketene dimer dispersions optionally comprise, based in each case on the ketene dimer,
(a) 0.1 to 10 wt % of aluminium sulfate, and/or
(b) 1 to 15 wt % of component (b), and/or
(c) 0.1 to 5 wt % of component (c), and/or
(d) 0.5 to 5 wt % of at least one saturated carboxylic acid having 1 to 10 C atoms, benzenesulfonic acid, p-toluenesulfonic acid and/or a mineral acid ($H_2SO_4$, $H_3PO_4$).

The disperse phase of the AKD dispersions generally has an average diameter of less than 10 µm, more particularly less than 5 µm, preferably less than 2 µm, more preferably less than 1 µm, very preferably less than 0.5 µm. In accordance with one of the following embodiments, the disperse phase of the ketene dispersions has an average diameter in the range from 0.5 to 10 µm, 0.5 to 5 µm, 1 to 10 µm, or 1 to 5 µm. The ketene dimer dispersion sizes reported here are weight-average sizes of the kind ascertainable by dynamic light scattering. Methods for doing this are familiar to the skilled person from—for example—H. Wiese in D. Distler, Wässrige Polymerdispersionen, Wiley-VCH 1999, section 4.2.1, p. 40ff and literature cited therein, and also H. Auweter, D. Horn, J. Colloid Interf. Sci. 105 (1985) 399, D. Lilge, D. Horn, Colloid Polym. Sci. 269 (1991) 704, or H. Wiese, D. Horn, J. Chem. Phys. 94 (1991) 6429.

The ketene dimers used have a melting point of approximately 45-70° C. Depending on temperature, therefore, the disperse phase may be present at least partly in liquid form. It is advantageous if the ketene dimers, following incorporation into the gypsum hemihydrate or anhydrite, as for example during the drying thereof, are exposed briefly (1 to 60 minutes) to a temperature above the melting point of the ketene dimer, and cool down again. In general the heat treatment takes place at a temperature in the range from 40 to 110° C., more particularly 50 to 100° C., and preferably 60 to 90° C.

It is preferred to use 0.02 to 8, preferably 0.1 to 5, more particularly 0.2 to 3 wt %, very preferably 0.5 to 2.5 wt %, of the ketene dimer, based on the mass of the dry gypsum hemihydrate or anhydrite.

In accordance with the invention the gypsum or the gypsum hemihydrate or anhydrite may comprise one or more components (additives) selected from cellulose ethers, such as methylhydroxypropylcellulose; slaked lime; mineral additives such as silica sand, limestone sand, limestone pebble, finely ground limestone, and clay minerals, such as mica, kaolinite, chrysoile, illite, smectite, vermiculite, talc, montmorillonite, hectorite, or saponite; low-density aggregates, such as perlite; fibers, such as cellulose fibers; fiber-containing components; accelerators, such as finely ground calcium sulfate dihydrate; thickeners such as starch and starch derivatives, guar derivatives, synthetic thickeners, polyacrylamides, and polyvinyl alcohols; retarders, such as a calcium salt of an N-polyoxymethylene-amino acid (Retardan P from Sika AG); air entrainers, such as fatty acids, alkyl sulfates, and phenyl ethoxylates; foaming agents, such as fatty alkyl sulfates and fatty alkyl ether sulfates; antifoam additives, such as silicones; swelling agents, such as phyllosilicates; polyacrylates; plasticizers, such as lignosulfonates, β-naphthalenesulfonates, melamine resins, phosphate- or phosphonate-containing structures, and polycarboxylate ethers; and stabilizers, such as starch and cellulose ethers. Said additives may be added at any time during or after step (a).

In the production of gypsum-containing foamed prefabricated building material, preferably fibers or a fiber-containing component may be included in the processing procedure. The fibers in question may be plant fibers, such as cellulose fibers, glass fibers, plastics fibers, mineral fibers, or metal fibers. The fiber-containing component may comprise sheetlike parts, such as card or paper. During the production of the gypsum-containing ready-made structural component, the fiber-containing component is generally applied at least to one of the surfaces or incorporated parallel to at least one of the surfaces. For this purpose the gypsum-containing composition of the invention may be applied to the fiber-containing component. In that case a fiber-containing component comprising microscopic fibers in sheetlike distribution is preferably used. A fiber-containing component of this kind may consist predominantly of paper or card, for example. The surfaces of the fiber-containing component may be pretreated before the gypsum is applied. It is preferred for a second fiber-containing component to be applied to the gypsum-containing composition which is applied to the fiber-containing component. In this way a three-ply layer is obtained, as in gypsum plasterboard panels, for example.

Alternatively the fiber-containing component can be incorporated in sheetlike manner into a gypsum-containing composition of the invention. In that case the fiber-containing component used preferably comprises macroscopic fibers in netlike disposition. A fiber-containing component of this kind may be constructed predominantly from cellulose fibers or glass fibers, for example. In this way a reinforced gypsum layer can be obtained, such as in gypsum fiberboard panels, for example.

Further, hydrophobized fibers or fiber-containing components may be used.

In step (ii) a foam is added. Preferably, the foam is a surfactant based foam and in particular an anionic surfactant-based foam. Suitable surfactants are $C_{12}$-$C_{20}$ alkylsulfates, $C_{12}$-$C_{20}$ alkylethersulfates, amphoteric surfactants (betaines), alkylpolyglycosides etc. the foam is prepared in a conventional manner, for example by means of a foam generator such as a rotor-stator system.

Preferably, a foam having a density of 50 to 300 g/l, preferably 60 to 250 g/l is used. The quantity of foam added is such that the prefabricated building material has a core density of <1.10 kg/dm$^3$, preferably <0.90 kg/dm$^3$, and in particular <0.80 kg/dm$^3$. According to an embodiment, the core density is 0.4 to 1.1, preferably 0.4 to 0.9 and more preferably 0.5 to 0.8 kg/dm$^3$. The production of a foamed prefabricated building material having a core density as indicated above is achieved by adding foam in a quantity such that the ratio of surfactant to gypsum hemihydrate or anhydrite is below 2.0 g, preferably 0.01 to 2.0 g surfactant per kg gypsum hemihydrate or anhydrite.

The components contained in the AKD dispersion may be admixed in any order, i.e. simultaneously or one after the other, each partly or completely. However, it is preferred to add component (c) to component (a) and thereafter add the alkyl ketene dimer. Further, the foam and gypsum hemihydrate or anhydrite may be added to the AKD dispersion in step (ii) in any order, i.e. simultaneously or one after the other, each partly or completely. Preferably, the gypsum hemihydrate or anhydrite is admixed with the AKD dispersion or a part thereof and the aqueous foam is then added to the mixture. According to another embodiment, the gypsum hemihydrate or anhydrite is admixed with the aqueous foam or a part thereof and the AKD dispersion is added to the mixture.

In step (iii) the gypsum composition is subjected to conventional processing steps, in particular forming the composition (slurry) to the desired shape and drying it. The curing process already starts during step (ii) and continues during shaping and drying. If desired, the curing process can be completed prior to drying the prefabricated building material. The foamed prefabricated building materials are dried, typically in a drying tunnel, at gypsum core temperatures in the range from 40 to 100° C., more particularly in the range from 60° C. to 90° C.

The present invention also relates to a gypsum-containing foamed prefabricated building material (ready-made structural components) obtainable by the method of the invention.

The following examples illustrate the invention without limiting it.

In the examples below the following AKD dispersions were used:

AKD Dispersion I (Comparative Dispersion):

Aqueous dispersion of a $C_{16}$/$C_{18}$ (50:50) alkylketene dimer (in formula I and II: $R^1$ and $R^2$ are $C_{14}$ and $C_{16}$ alkyl, respectively) dispersed with 3 wt % of a highly cationically modified, low viscosity starch and 1 wt % of the sodium salt of the condensation product of naphthalenesulfonic acid with formaldehyde (Tamol NN 7718). The average particle diameter is about 2000 nm. The total solids content is about 24%.

AKD Dispersion II (Comparative Dispersion):

Aqueous dispersion of a $C_{16}$/$C_{18}$ (20:80) alkylketene dimer (in formula I and II: $R^1$ and $R^2$ are $C_{14}$ and $C_{16}$ alkyl, respectively) dispersed with 3 wt % of a highly cationically modified, low viscosity starch) and 1 wt % of the sodium salt of the condensation product of naphthalenesulfonic acid with formaldehyde (Tamol NN 7718). The average particle diameter is about 2000 nm. The total solids content is about 18%.

AKD Dispersion III (According to the Invention):

Aqueous dispersion of a C16/C18 (50:50) alkylketene dimer (in formula I and II: $R^1$ and $R^2$ are $C_{14}$ and $C_{16}$ alkyl, respectively) dispersed with 3 wt % of a nonionic, low-viscosity starch (Amylex 15 of Südstärke; nitrogen content <0.10% by weight; Brookfield viscosity 16.5 mPas) and 1 wt % of the sodium salt of the condensation product of naphthalenesulfonic acid and formaldehyde (Tamol NN 7718; commercially available from BASF SE). The average particle diameter is about 2000 nm. The total solids content is about 24%.

AKD Dispersion IV (According to the Invention):

Aqueous dispersion of a C16/C18 (50:50) alkylketene dimer (in formula I and II: $R^1$ and $R^2$ are $C_{14}$ and $C_{16}$ alkyl, respectively) dispersed with 3 wt % of a nonionic, low-viscosity starch (Amylex 15 of Südstärke; nitrogen content <0.10% by weight; Brookfield viscosity 16.5 mPas) and 1 wt % of the sodium salt of the condensation product of phenolsulfonic acid and formaldehyde, phenol and urea (Tamol NN 7718; commercially available from BASF SE). The average particle diameter is about 2000 nm. The total solids content is about 24%.

AKD Dispersion V (According to the Invention):

Aqueous dispersion of a C16/C18 (50:50) alkylketene dimer (in formula I and II: $R^1$ and $R^2$ are $C_{14}$ and $C_{16}$ alkyl, respectively) dispersed with 3 wt % of a nonionic, low-viscosity starch (Amylex 15 of Südstärke; nitrogen content <0.10% by weight; Brookfield viscosity 16.5 mPas) and 1 wt % of the sodium salt of the condensation product of naphthalenesulfonic acid and formaldehyde (Tamol NN 7718; commercially available from BASF SE). Moreover 0.4% of solvent (fatty alcohol ethoxylate; Degressal SD 21) were added to aqueous dispersion and homogenized. The average particle diameter is about 2000 nm. The total solids content is about 24.4%.

Wax Dispersion VI (Comparative Dispersion):

Aqueous dispersion of a paraffin wax (melting point=50-52° C.) dispersed with 3 wt % of a nonionic, low-viscosity starch (Amylex 15 of Südstärke; nitrogen content <0.10% by weight; Brookfield viscosity 16.5 mPas) and 1 wt % of the sodium salt of the condensation product of naphthalenesulfonic acid and formaldehyde (Tamol NN 7718; commercially available from BASF SE). The average particle diameter is about 2000 nm. The total solids content is about 35%.

AKD Dispersion VII (According to the Invention):

Aqueous dispersion of a C16/C18 (50:50) alkylketene dimer (15.5%) (in formula I and II: $R^1$ and $R^2$ are $C_{14}$ and $C_{16}$ alkyl), respectively, and a paraffin wax, having a melting point of 50-52° C. (15.5%) dispersed with 3 wt % of a nonionic, low-viscosity starch (Amylex 15 of Südstärke; nitrogen content <0.10% by weight; Brookfield viscosity 16.5 mPas) and 1 wt % of the sodium salt of the condensation product of naphthalenesulfonic acid and formaldehyde (Tamol NN 7718; commercially available from BASF SE). The average particle diameter is about 2000 nm. The total solids content is about 35%.

EXAMPLE 1 (COMPARATIVE)

A fatty alkyl sulfate-based foam was produced as follows: A 0.3% strength surfactant solution (based on lauryl sulfate) was converted into foam in a foam generator by rotation of a stator-rotor system (Hobart mixer) and with addition of compressed air. The foam density achieved was 75 g/L.

A gypsum slurry was prepared by introducing 600 g of gypsum β-hemihydrate obtained from flue gas desulfurization) and 0.16 g of accelerator (finely ground calcium sulfate dihydrate for setting a solidification time) into 443.8 g of water, and the mixture was left at rest for 15 seconds. The Hobart mixer was then used on setting II (285 revolutions per minute) for 30 seconds, and during this stirring time the fatty alkyl ether sulfate-based foam (27.2 g with a density of 75 g/L) was admixed, until the resulting gypsum slurry had a fresh density of 1050+/20 kg/m$^3$.

EXAMPLE 2 (COMPARATIVE EXAMPLE)

A diluted AKD dispersion was prepared by weighing out 30.0 g of the 24% AKD dispersion I into 420.9 g of water. Then 600 g of gypsum (β-hemihydrate obtained from flue gas desulfurization) and 0.16 g of accelerator (finely ground calcium sulfate dihydrate for setting a solidification time) were introduced into the diluted AKD dispersion I, and the mixture was left at rest for 15 seconds. A Hobart mixer was then used on setting II (285 revolutions per minute) for 30 seconds, and during this stirring time the fatty alkyl ether sulfate-based foam (27.2 g with a density of 75 g/L) was admixed, until the resulting gypsum slurry had a fresh density of 1050+/20 kg/m$^3$.

EXAMPLE 3 (ACCORDING TO THE INVENTION)

A gypsum slurry was prepared in the same way as in example 2 by using 30 g of AKD dispersion III instead of 30 g AKD dispersion I.

The following experiments were carried out with the gypsum slurries of examples 1 to 3:

Determination of Initial Setting:

Initial setting was determined with the so-called knife-cut method (analogous to DIN EN 13279-2)

Determination of Flow:

Flow was determined after a time of 60 seconds. After mixing at a total time of 45 seconds a cylinder (d=5 cm and h=10 cm) was filled with the slurry up to the top edge and lifted after 60 seconds. At the end the patty diameter was measured with a caliper rule on two perpendicular axes.

The results are shown in table 1 below:

TABLE 1

Slump flows and initial setting times

| Parameter | Slump flow [cm] | Solidification time [min:s] |
|---|---|---|
| Example 1 (Comparative) | 18.1 | 2:10 |
| Example 2 (Comparative) | 15.6 | 2:05 |
| Example 3 (Invention) | 20.5 | 2:10 |

Table 1 shows that use of a low cationically charged starch (example 3) leads to improved flow. This is achieved without impact on setting.

EXAMPLE 4 (ACCORDING TO THE INVENTION)

A gypsum slurry was prepared in the same way as in example 2 by using 30 g of AKD dispersion IV instead of 30 g AKD dispersion I.

Slump flow and initial setting times of the gypsum slurries of examples 1, 3 and 4 were determined as described above. The results are given in table 2 below:

TABLE 2

Slump flows and initial setting times

| Parameter | Slump flow [cm] | Solidification time [min:s] |
|---|---|---|
| Example 1 (Comparative) | 18.1 | 2:10 |
| Example 3 (Invention) | 20.5 | 2:10 |
| Example 4 (Invention) | 23.0 | 2:15 |

Table 2 shows that the flow behavior could be further improved without negative impact on setting when using the sodium salt of the condensation product of phenolsulfonic acid with formaldehyde, phenol and urea (example 4) instead of the sodium salt of the condensation product of naphthalenesulfonic acid with formaldehyde (example 3) as a dispersant in AKD emulsions.

In addition, the water uptake of test specimens prepared from the slurries of examples 3 and 4 was determined as follows:

The dispersion of the hydrophobizing agent was diluted with water in a vessel and homogenized to form a liquid component, to give the amounts of hydrophobizing agent indicated in table 3 below in 443.8 g of water—in other words, the water present in the hydrophobizing agent dispersion was included in the calculation. β-Hemihydrate (600 g) obtained in flue gas desulfurization was subjected to preliminary homogenization with 0.16 g of finely ground calcium sulfate dihydrate (accelerator for setting a solidification time of about 2.5 minutes) in a mixer to give a dry component. The dry component was sprinkled into the liquid component. After standing for 15 seconds, the resulting gypsum slurry was stirred using a Hobart mixer at setting II (285 revolutions per minute) for 30 seconds, and during this stirring time the fatty alkyl sulfate-based foam (27.2 g with a density of 75 g/L) was admixed. The density of the resulting gypsum slurry was 1050+/−20 kg/m³. Filling of a cylindrical plastic beaker with a height of 10 cm and a diameter of 8 cm with a portion of the gypsum slurry was followed by curing and drying to form a specimen having a height of about 2 cm. After the specimen has hardened (storage at 20° C. for 15 minutes) it is removed from the plastic mold and dried at 100° C. for 15 minutes and then at around 40° C. to constant mass. The mass of the specimen ($M_D$) was ascertained by weighing. For the measurement of the water adsorption, the specimen was stored in a water bath at a set temperature of 20° C. The fill level of the water bath was set such that the highest point on the specimen was covered by 3 cm of water. After water bath storage for two hours, the specimen was removed from the water bath, and excess water was removed using a cloth. The mass of the specimen ($M_W$) was ascertained again by weighing, and the water uptake W in % was determined in accordance with the following formula:

$$W = 100\% \times ((M_W - M_D)/M_D)$$

The results are given in table 3 below:

TABLE 3

Water uptake of specimens following addition of different hydrophobizing agents and different amounts of hydrophobizing agent

| Hydrophobizing agent | Water absorption (mass %) | |
|---|---|---|
| (mass % based on β-hemihydrate) | Example 3 | Example 4 (invention) |
| 0 | 57.8 | 57.8 |
| 0.7 | 13.2 | 4.2 |
| 0.85 | 6.6 | 2.9 |
| 1.0 | 3.7 | 2.6 |

From table 3 can be seen that for a water uptake of less than 5 wt % it is necessary to add more than 0.85 wt % of the AKD dispersion III, whereas with AKD dispersion IV (with Tamol DN) this figure is already achieved with an addition of less than 0.7 wt %.

EXAMPLE 5 (ACCORDING TO THE INVENTION)

A gypsum slurry was prepared in the same way as in example 2 by using 21.60 g of AKD dispersion III instead of 30 g AKD dispersion I.

EXAMPLE 6 (ACCORDING TO THE INVENTION)

A gypsum slurry was prepared in the same way as in example 2 by using 21.96 g of AKD dispersion V instead of 30 g AKD dispersion I.

Slump flows and initial setting times were determined as described above. The results are given in table 4 below:

TABLE 4

Slump flows and initial setting times of examples 5 and 6.

| Parameter | Slump flow [cm] | Solidification time [min:s] |
|---|---|---|
| Example 5 (invention) | 20.9 | 2:40 |
| Example 6 (invention) | 25.1 | 2:45 |

Table 4 shows that by use of a solvent (fatty alcohol ethoxylate) the slump flow could be further improved without influencing the setting time.

In addition, test specimens were prepared and the water uptake thereof was determined as described above using the slurries of examples 3 and 6. The results are given in table 5 below:

TABLE 5

Water uptake of specimens following addition of different hydrophobizing agents and different amounts of hydrophobizing agent

| Hydrophobizing agent | Water absorption (mass %) | |
|---|---|---|
| (mass % based on β-hemihydrate) | Example 3 | Example 6 (invention) |
| 0 | 53.2 | 53.2 |
| 0.6 | 10.8 | 5.7 |
| 0.8 | 3.2 | 1.5 |
| 1.0 | 1.2 | 1.1 |

Table 5 shows that water uptake is reduced by addition of solvent (fatty alcohol ethoxylate). All measured water adsorptions with the slurry of example 6 were lower than for the slurry of example 3.

EXAMPLE 7 (COMPARATIVE EXAMPLE)

Test specimens were prepared as described above using wax dispersion VI.

EXAMPLE 8 (ACCORDING TO THE INVENTION)

Test specimens were prepared and the water uptake determined as described above using AKD dispersion VII. The results are given in table 6 below:

TABLE 6

Water uptake of specimens following addition of different hydrophobizing agents and different amounts of hydrophobizing agent according to example 4.

| Hydrophobizing agent | Water absorption (mass %) | |
| --- | --- | --- |
| (mass % based on β-hemihydrate) | Example 7 | Example 8 (invention) |
| 0 | 53.2 | 53.2 |
| 0.6 | 44.6 | 38.2 |
| 0.8 | 44.3 | 28.4 |
| 1.0 | 44.0 | 18.5 |
| 1.2 | 44.4 | 10.3 |
| 1.6 | 47.3 | 3.7 |

Table 6 shows that pure paraffin wax dispersions are not able to achieve water adsorptions below 5% inspite of the presence of the condensation product of naphthalenesulfonic acid and formaldehyde. Even at dispersion dosages of 1.6% by weight stucco the water adsorption was higher than 40%. By use of a mixture of AKD and paraffin wax it is possible to achieve water adsorption values below 5%. For example 8 about 0.6% of AKD/paraffin wax emulsion were enough to achieve water adsorption values below 40%.

Comparative AKD Dispersion VIII (Comparative Dispersion):

Aqueous dispersion of a $C_{16}/C_{16}$ (50:50) alkylketene dimer dispersed with 3 wt % of a highly cationic modified, low-viscose starch (in formula I and II: $R^1$ and $R^2$ are $C_{14}$ and $C_{16}$ alkyl, respectively) and 1 wt % of the sodium salt of the condensation product of naphthalenesulfonic acid with formaldehyde (Tamol NN 7718). The average particle diameter is about 1000 nm. The charge density of the dispersion is about +77 µeq/g. The total solids content is about 24%.

AKD Dispersion IX (According to the Invention):

Aqueous dispersion of a $C_{16}/C_{16}$ (50:50) alkylketene dimer (in formula I and II: $R^1$ and $R^2$ are $C_{14}$ and $C_{16}$ alkyl, respectively) dispersed with 2 wt % of a highly cationically modified, low viscosity starch) and 2 wt % of the sodium salt of the condensation product of naphthalenesulfonic acid with formaldehyde (Tamol NN 7718). The average particle diameter is about 1000 nm. The viscosity is about 10 mPas (Method: Brookfield, RVDV-II+PX, spindle 01, 6 rpm, 20° C.). The charge density of the dispersion is about −80 µeq/g. The total solids content is about 20%.

EXAMPLE 9 (COMPARATIVE EXAMPLE)

A diluted AKD dispersion was prepared by weighing out 30.0 g of the 24% AKD dispersion VIII into 420.9 g of water. Then 600 g of gypsum (β-hemihydrate obtained from flue gas desulfurization) and 0.16 g of accelerator (finely ground calcium sulfate dihydrate for setting a solidification time) were introduced into the diluted AKD dispersion I, and the mixture was left at rest for 15 seconds. A Hobart mixer was then used on setting II (285 revolutions per minute) for 30 seconds, and during this stirring time the fatty alkyl ether sulfate-based foam (27.2 g with a density of 75 g/L) was admixed, until the resulting gypsum slurry had a fresh density of 1050+/20 kg/m³.

EXAMPLE 10 (ACCORDING TO THE INVENTION)

A gypsum slurry was prepared in the same way as in example 1 by using 37.5 g of AKD dispersion IX in 413.7 g of water.

Test samples were prepared from the gypsum slurries of examples 1 and 2 and the water-uptake of the samples in [mass %] was determined in accordance with DIN EN 520. The result are given in the following table:

| Hydrophobizing agent | Water absorption (mass %) | |
| --- | --- | --- |
| (mass % based on β-hemihydrate) | Example 9 | Example 10 (invention) |
| 0 | 57.8 | 57.8 |
| 0.55 | 36.7 | 23.3 |
| 0.70 | 13.5 | 7.8 |

As can be seen, the water uptake is reduced by use of anionically charged AKD emulsion (charge density in the range from −5 to −150 µeq/g). All measured values were lower with the example of the invention in comparison to those for example 9.

The invention claimed is:
1. An aqueous alkyl ketene dimer dispersion comprising
   (a) an alkyl ketene dimer of the formula (I)

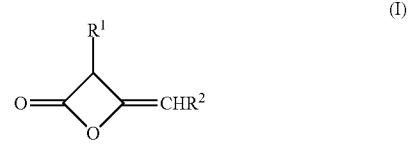

and/or of the formula (II)

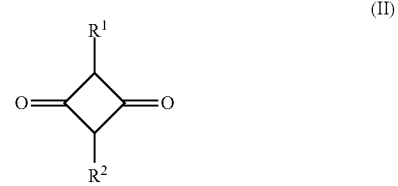

in which
   $R^1$ and $R^2$ are identical or different hydrocarbon radicals comprising 10 to 24 carbon atoms;
   (b) at least one emulsifier having a nitrogen content in the range from 0.05 to 1% by weight and a Brookfield viscosity (20° C.; spindle 61 or 62; 12 rpm) in the range from about 10 to about 500 mPas in a 10% w/w aqueous solution, the emulsifier being selected from the group consisting of a starch, cellulose, starch derivative and cellulose derivative;

(c) a condensation product of phenol sulfonic acid and formaldehyde, naphthalene sulfonic acid and formaldehyde or naphthalene sulfonic acid, phenol, formaldehyde and urea wherein sulfonic acid groups of the phenol sulfonic acid and the naphthalene sulfonic acid may optionally be present in protonated or deprotonated or partly in protonated and partly in deprotonated form;

wherein the dispersion has a charge density in the range from −5 to −150 µeq/g.

2. The dispersion of claim 1 having a charge density in the range from −10 to −120 µeq/g.

3. The dispersion of claim 1, wherein the at least one emulsifier has a nitrogen content in the range from 0.2 to 0.8% by weight.

4. The dispersion of claim 1, which additionally comprises at least one fatty alcohol alkoxylate, fatty amine alkoxylate or fatty acid alkoxylate.

5. The dispersion of claim 4, wherein the fatty alcohol alkoxylate is a $C_8$-$C_{18}$ alkanol ethoxylate with 10 to 30 ethylene oxide groups.

6. The dispersion of claim 1, which additionally comprises a wax.

7. The dispersion of claim 1, in the form of a gypsum composition which dispersion additionally comprises gypsum hemihydrate or anhydrite or a mixture thereof.

8. The dispersion of claim 7, wherein the gypsum hemihydrate or anhydrite is selected from α-hemihydrate, α/β-hemihydrate, β-hemihydrate, natural anhydrite, synthetic anhydrite, anhydrite obtained from flue gas desulfurization, and/or mixtures of two or more thereof.

9. The dispersion of claim 7, which additionally comprises an aqueous foam.

10. The dispersion of claim 9, wherein a foam having a density from about 50 to 300 g/l is used.

11. The dispersion of claim 10, wherein the foam is obtained from 0.01 to 2 g surfactant per kg gypsum hemihydrate or anhydrite.

12. A method for producing a gypsum-containing foamed prefabricated building material comprising the steps of
(a) providing the dispersion in the form of a gypsum composition additionally comprising an aqueous foam as defined in claim 9; and
(b) forming, optionally curing and drying the gypsum composition to obtain the foamed prefabricated building material.

13. The method of claim 12, wherein the gypsum composition is obtained by adding the alkylketene dimer of the formula (I) or (II) to components (b) and (c) of the dispersion and then adding the foam.

14. The method of claim 13, wherein the alkyl ketene dimer is employed in the form of an aqueous dispersion.

15. The method of claim 14, wherein the aqueous alkyl ketene dispersion comprises 1 to 60 wt % of ketene dimer, based on the total weight of the dispersion.

16. The method of claim 12, wherein 0.02 to 8.0 wt %, of the alkyl ketene dimer, based on the weight of the gypsum hemihydrate or anhydrite, is used.

17. A prefabricated construction chemical building material comprising a gypsum body hydrophobized with the dispersion of claim 7.

18. A gypsum-containing prefabricated building material obtained from the dispersion according to claim 7.

19. The building material of claim 17 wherein the gypsum body has a core density of 0.4 to 1.1 kg/dm³.

20. The building material of claim 17 selected from gypsum plasterboard panels, gypsum fiberboard panels, gypsum-containing wallboarding panels, and gypsum-containing moldings.

21. A gypsum-containing foamed prefabricated building material, comprising a gypsum body hydrophobized with the dispersion of claim 9.

* * * * *